US012714665B2

United States Patent
(12) United States Patent
Bleiel et al.

(10) Patent No.: US 12,714,665 B2
(45) Date of Patent: Aug. 25, 2026

(54) METHOD OF REDUCING FOOD INTAKE IN A HEALTHY MAMMAL

(71) Applicant: AnaBio Technologies Ltd., County Cork (IE)

(72) Inventors: Sinead Bleiel, Dublin (IE); Robert Kent, Cork (IE); Neil Gerard Docherty, Dublin (IE); Carel Wynand Le Roux, Dublin (IE)

(73) Assignee: TEAGASC—THE AGRICULTURE AND FOOD DEVELOPMENT AUTHORITY, Carlow (IE)

( * ) Notice: Subject to any disclaimer, the term of this patent is extended or adjusted under 35 U.S.C. 154(b) by 720 days.

(21) Appl. No.: 16/978,421

(22) PCT Filed: Mar. 7, 2019

(86) PCT No.: PCT/EP2019/055791
§ 371 (c)(1),
(2) Date: Sep. 4, 2020

(87) PCT Pub. No.: WO2019/170839
PCT Pub. Date: Sep. 12, 2019

(65) Prior Publication Data

US 2021/0077386 A1 Mar. 18, 2021

(30) Foreign Application Priority Data

Mar. 7, 2018 (GB) ..................................... 1803664

(51) Int. Cl.
*A61K 9/00* (2006.01)
*A23L 2/66* (2006.01)
(Continued)

(52) U.S. Cl.
CPC .............. *A61K 9/0053* (2013.01); *A23L 2/66* (2013.01); *A23L 33/115* (2016.08); (Continued)

(58) Field of Classification Search
None
See application file for complete search history.

(56) References Cited

U.S. PATENT DOCUMENTS 12,616,661 B2 5/2026 Bleiel et al.
2021/0100749 A1 4/2021 Bleiel et al.
2022/0040258 A1 2/2022 Bleiel

FOREIGN PATENT DOCUMENTS

CA 2654031 A1 * 2/2008 ................ A61P 9/12
CN 107405310 A 11/2017
(Continued)

OTHER PUBLICATIONS

Welch et al. (Effect of ileal and intravenous infusions of fat emulsions on feeding and satiety in human volunteers, Gastroenterology, vol. 89, Issue 6, Dec. 1985, pp. 1293-1297) (Year: 1985).*
(Continued)

*Primary Examiner* — Melissa S Mercier
(74) *Attorney, Agent, or Firm* — HAMILTON, BROOK, SMITH & REYNOLDS, P.C.

(57) ABSTRACT

A therapeutic or non-therapeutic method of inducing satiety in a mammal is described. The method comprises administering to the mammal a composition comprising microparticles, in which the microparticles comprise lipid contained within a gastric-resistant, ileal-sensitive, carrier configured for release of the lipid in the ileum, wherein the composition is administered 1-3 hours prior to a meal. The carrier is a protein, typically denatured or hydrolysed plant or dairy protein, that is polymerised to form a lipid containing shell or matrix.

14 Claims, 10 Drawing Sheets

(51) Int. Cl.

| | |
|---|---|
| *A23L 33/00* | (2016.01) |
| *A23L 33/115* | (2016.01) |
| *A23L 33/185* | (2016.01) |
| *A23L 33/19* | (2016.01) |
| *A23P 10/35* | (2016.01) |
| *A61K 9/48* | (2006.01) |
| *A61K 9/50* | (2006.01) |
| *A61K 31/202* | (2006.01) |
| *A61P 3/04* | (2006.01) |

(52) U.S. Cl.

CPC ............. *A23L 33/185* (2016.08); *A23L 33/19* (2016.08); *A23L 33/40* (2016.08); *A23P 10/35* (2016.08); *A61K 9/4808* (2013.01); *A61K 9/5052* (2013.01); *A61K 9/5089* (2013.01); *A61K 31/202* (2013.01); *A61P 3/04* (2018.01); *A23V 2002/00* (2013.01)

(56) References Cited

FOREIGN PATENT DOCUMENTS

| | | | | |
|---|---|---|---|---|
| WO | 2004105520 | A1 | 12/2004 | |
| WO | 2009053487 | A2 | 4/2009 | |
| WO | 2010/027498 | A2 | 3/2010 | |
| WO | 2010/119041 | A2 | 10/2010 | |
| WO | 2013/063527 | A1 | 5/2013 | |
| WO | 2014198787 | A1 | 12/2014 | |
| WO | 2016020217 | A1 | 2/2016 | |
| WO | 2016/096929 | A1 | 6/2016 | |
| WO | 2016096931 | A1 | 6/2016 | |
| WO | 2016/178202 | A1 | 11/2016 | |
| WO | 2016/185053 | A1 | 11/2016 | |
| WO | 2016/205754 | A1 | 12/2016 | |
| WO | WO-2016193373 | A1 * | 12/2016 | ............. A23P 10/30 |
| WO | WO20160193373 | * | 12/2016 | |
| WO | 2019/170839 | A2 | 9/2019 | |
| WO | 2019/170840 | A1 | 9/2019 | |

OTHER PUBLICATIONS

International Search Report and Written Opinion for Int'l Application No. PCT/EP2019/055792, titled: A Composition for Type II Diabetics and for Use in Providing Sustained Energy Release Over Time, Date Mailed: Jul. 24, 2019.

International Preliminary Report on Patentability for Int'l Application No. PCT/EP2019/055792, titled: A Composition for Type II Diabetics and for Use in Providing Sustained Energy Release Over Time, Date of Issuance: Sep. 8, 2020.

Adrian TE, Long RG, Fuessl HS, Bloom SR. Plasma peptide YY (PYY) in dumping syndrome. Dig Dis Sci. 1985;30(12):1145-8.

Anal AK, Singh H. Recent advances in microencapsulation of probiotics for industrial applications and targeted delivery. Trends Food Sci Technol. 2007;18(5):240-251.

Aponte, G.W. et al., "Primary culture of PPY cells from canine colon," Am J Physiol. 1988;254(6): G829-G836.

Batterham, R.L. et al., "Critical role for peptide YY in protein-mediated satiation and body-weight regulation," Cell Metabolism, vol. 4; 223-233 (2006).

Burns AA, Livingstone MB, Welch RW, Dunne A, Reid CA, Rowland IR. The effects of yoghurt containing a novel fat emulsion on energy and macronutrient intakes in non-overweight, overweight and obese subjects. Int J Obes Relat Metab Disord. 2001;25(10):1487-96.

Burns AA, Livingstone MB, Welch RW, Dunne A, Robson PJ, Lindmark L, Reid CA, Mullaney U, Rowland IR. Short-term effects of yoghurt containing a novel fat emulsion on energy and macronutrient intakes in non-obese subjects. Int J Obes Relat Metab Disord. 2000;24(11):1419-25.

Burns AA, Livingstone MB, Welch RW, Dunne A, Rowland IR. Dose-response effects of a novel fat emulsion (Olibra) on energy and macronutrient intakes up to 36 h post-consumption. Eur J Clin Nutr. 2002;56(4):368-77.

Chan YK, Strik CM, Budgett SC, McGill AT, Proctor J, Poppitt SD. The emulsified lipid Fabuless (Olibra) does not decrease food intake but suppresses appetite when consumed with yoghurt but not alone or with solid foods: a food effect study. Physiol Behav. 2012;105(3):742-8.

Choi CH, Jung JH, Rhee YW, Kim DP, Shim SE, Lee CS. Generation of monodisperse alginate microbeads and in situ encapsulation of cell in microfluidic device. Biomed Microdevices. 2007;9(6):855-62.

FAO, Chapter 3, FAO Food and Nutrition Paper 77, Food Energy—methods of analysis and conversion factors, Food and Agriculture Organization of the United Nations, 21 pages. (Year: 2003).

International Preliminary Report on Patentability for Int'l Application No. PCT/EP2019/055791, titled: A Method Inducing Satiety in a Mammal, Date of Issuance: Sep. 8, 2020.

Kuhre et al, Fructose stimulates GLP-1 but not GIP secretion in mice, rats, and humans, 2014, Am J Physiol Gastroinest Liver Physiol., 306(7): G622-G630, 16 pages. (Year: 2014).

Lin HC, Zhao XT, Wang L, Wong H. Fat-induced ileal brake in the dog depends on peptide YY. Gastroenterology. 1996;110(5):1491-5.

Lin HC, Zhao XT, Wang L. Intestinal transit is more potently inhibited by fat in the distal (ileal brake) than in the proximal (jejunal brake) gut. Dig Dis Sci. 1997;42(1):19-25.

Logan CM, McCaffrey TA, Wallace JM, Robson PJ, Welch RW, Dunne A, Livingstone MB. Investigation of the medium-term effects of Olibra™ fat emulsion on food intake in non-obese subjects. Eur J Clin Nutr. 2006;60 (9):1081-91.

Maljaars, P.W.J. et al., "Length and site of the small intestine exposed to fat influences hunger and food intake," British Journal of Nutrition, vol. 106; 1609-1615 (2011).

Minekus, M. et al., "A computer-controlled system to simulate conditions of the large intestine with peristaltic mixing, water absorption and absorption of fermentation products," Appl. Microbiol. Biotechnol., vol. 53; 108-114 (1999).

Minekus, M. et al., "A Standardised static in vitro digestion method suitable for food—an international consensus," Food Funct., vol. 5; 1113; 12 pages (2014).

Nazzaro F, Orlando P, Fratianni F, Coppola R. Microencapsulation in food science and biotechnology. Curr Opin Biotechnol. 2012;23(2):182-6.

Non-Final Office Action received for U.S. Appl. No. 16/978,587, mailed on Feb. 22, 2024, 8 pages.

Pironi, L. et al., "Fat-Induced Ileal Brake in Humans: A Dose-Dependent Phenomenon Correlated to the Plasma Levels of Peptide YY," Gastroenterology, vol. 105; 733-739 (1993).

Ramadan, M. et al., "Risk of Dumping Syndrome after Sleeve Gastrectomy and Roux-en-Y Gastric Bypass: Early Results of a Multicentre Prospective Study," Gastroenterology Research and Practice, vol. 2016, Article ID 2570237; 5 pages (2016).

Rudnicki M, Kuvshinoff BW, McFadden DW. Extrinsic neural contribution to ileal peptide YY (PYY) release. J Surg Res. 1992;52(6):591-5.

Smit HJ, Keenan E, Kovacs EM, Wiseman SA, Peters HP, Mela DJ, Rogers PJ. No efficacy of processed Fabuless (Olibra) in suppressing appetite or food intake. Eur J Clin Nutr. 2011;65(1):81-6.

Spiller RC, Trotman IF, Higgins BE, Ghatei MA, Grimble GK, Lee YC, Bloom SR, Misiewicz JJ, Silk DB. The ileal brake—inhibition of jejunal motility after ileal fat perfusion in man. Gut. 1984;25(4):365-74.

Van Avesaat M, Ripken D, Hendriks HF, Masclee AA, Troost FJ. Small intestinal protein infusion in humans: evidence for a location-specific gradient in intestinal feedback on food intake and GI peptide release. Int J Obes (Lond). 2017;41(2):217-224.

Van Beek, A.P. et al., "Dumping syndrome after esophageal, gastric or bariatric surgery: pathophysiology, diagnosis, and management," Obesity, vol. 18; 68-85 (2017).

Van Citters GW, Lin HC. Ileal brake: neuropeptidergic control of intestinal transit. Curr Gastroenterol Rep. 2006;8(5):367-73.

(56) References Cited

OTHER PUBLICATIONS

Varum FJ, Hatton GB, Freire AC, Basit AW. A novel coating concept for ileo-colonic drug targeting: proof of concept in humans using scintigraphy. Eur J Pharm Biopharm. 2013;84(3):573-7.
Vincent RP, Ashrafian H, le Roux CW. Mechanisms of disease: the role of gastrointestinal hormones in appetite and obesity. Nat Clin Pract Gastroenterol Hepatol. 2008;5(5):268-77.
Welch IM, Sepple CP, Read NW. Comparisons of the effects on satiety and eating behaviour of infusion of lipid into the different regions of the small intestine. Gut. 1988;29(3):306-11.
Welch, I. et al., "Effect of Ileal and Intravenous Infusions of Fat Emulsions on Feeding and Satieety in Human Volunteers," Gastroenterology, vol. 89; 1293-1297 (1985).
Woltman T, Reidelberger R. Effects of duodenal and distal ileal infusions of glucose and oleic acid on meal patterns in rats. Am J Physiol. 1995;269(1):R7-14.
Diepvens, K. et al., "Short-term effects of a novel fat emulsion on appetite and food intake," Physiology & Behavior; vol. 95; 114-117 (2008).
Final Office Action received for U.S. Appl. No. 16/978,587, mailed on Aug. 28, 2024, 7 pages.
Schellekens, R.C.A. et al., "Oral ileocolonic drug delivery by the colopulse-system: A bioavailability study in healthy volunteers," Journal of Controlled release, vol. 146; 334-340 (2010).
Non-Final Office Action received for U.S. Appl. No. 16/978,587, mailed on Feb. 13, 2025, 8 pages.
Jens Juul Holst et al., Actions of glucagon-like peptide-1 receptor ligands in the gut, Br J Pharmacol. 2022, 727-742, 179.
Lin et al, Gastric Emptying of Solid Food Is Most Potently Inhibited by Carbohydrate in the Canine Distal Ileum, 1992, Gastroenterology, 102, 792-801. (Year: 1992).
Final Office Action received for U.S. Appl. No. 16/978,587, mailed on Sep. 5, 2025, 13 pages.
Notice of Allowance received for U.S. Appl. No. 16/978,587, mailed on Jan. 6, 2026, 12 pages.
International Search Report and Written Opinion for Int'l Application No. PCT/EP2019/055791, titled: A Method Inducing Satiety in a Mammal, Date Mailed: Sep. 4, 2019.
Alleleyn, A. et al., "Gastrointestinal Nutrient Infusion Site and Eating Behavior: Evidence for a Proximal to Distal Gradient within the Small Intestine?" Nutrients, 8(3): 117 (Feb. 2016).
Alleleyn, A. et al., "The Effect of an Encapsulated Nutrient Mixture on Food Intake and Satiety: A Double-Blind Randomized Cross-Over Proof of Concept Study," Nutrients, 10(11): 1787 (Nov. 2018).
Van Avesaat, M. et al., "Ileal Brake Activation: Macronutrient-Specific Effects on Eating Behavior?" International Journal of Obesity, 39(2): 235-243 (Feb. 2015).
Yoder, S.M. et al., "Stimulation of Incretin Secretion by Dietary Lipid: Is it Dose Dependent?" American Journal of Physiology—Gastrointestinal and Liver Physiology, 297(2): G299-G305 (Aug. 2009).

* cited by examiner

FIGURE 2

| Time | Trial 1<br>(n=8) | Trial 2<br>(n= 72) |
|---|---|---|
| 08:00 | Subject Arrives fasted | |
| 08:05 | Body Measurements | Body Measurements |
| 08:10 | Fasting Visual Analogue Scale (VAS) | Fasting Visual Analogue Scale (VAS) |
| 08:15 | Baseline Blood draw | Baseline Blood draw |
| 08:20 | Consumption of Lipid Microparticulate Drink<br>(10 minutes) | Consumption of Lipid Microparticulate Drink<br>(10 minutes) |
| 09:00 | VAS and Blood Draws 1 | VAS and Blood Draws 1 |
| 09:30 | VAS and Blood Draws 2 | VAS and Blood Draws 2 |
| 10:00 | VAS and Blood Draws 3 | VAS and Blood Draws 3 |
| 10:30 | VAS and Blood Draws 4 | VAS and Blood Draws 4 |
| 11:00 | VAS and Blood Draws 5 | VAS and Blood Draws 5 |
| 11:30 | VAS and Blood Draws 6 | VAS and Blood Draws 6 |
| 11:35 | Ad Libitum meal | Ad Libitum meal |
| 11:55 | Subjects leaves | Subjects leaves |
| | | |

Fat 15
10
5
0

Glucose (mmol/L)

0 30 60 90 120 150 180

Minutes

Fat Stomach
Fat Distal Bowel

FIGURE 3

METHOD OF REDUCING FOOD INTAKE IN A HEALTHY MAMMAL

This application is the U.S. National Stage of International Application No. PCT/EP2019/055791, filed on Mar. 7, 2019, which designates the U.S., published in English, and claims priority under 35 U.S.C. § 119 or 365(c) to Great Britain Application No. 1803664.0, filed on Mar. 7, 2018. The entire teachings of the above applications are incorporated herein by reference.

FIELD OF THE INVENTION

The present invention relates to a method of inducing satiety in a mammal. The invention also relates to a method of regulating food intake in a mammal, especially an obese mammal. The invention also relates to a method of treating or preventing obesity in a mammal, especially an obese mammal.

BACKGROUND TO THE INVENTION

The worldwide, rapidly increasing prevalence of overweight and obesity has triggered research into food or food products that have therapeutic potential in the management of overweight, obesity, and associated diseases. For example, so-called functional foods containing nutrients that cause larger reductions in food intake than would be expected on the basis of their caloric contents alone. These functional foods may have a role in dieting plans to improve compliance by reducing between-meal hunger, generating gut peptide hormone responses, postponing subsequent meal consumption and reducing caloric intake. Recent studies have shown that under normal physiological situations, undigested nutrients can reach the ileum, and induce activation of the so-called “ileal brake”, a combination of effects influencing digestive process and ingestive behaviour. The relevance of the ileal brake as a potential target for weight management is based on several findings: First, activation of the ileal brake has been shown to reduce food intake and increase satiety levels. Second, surgical (bariatric) procedures that increase exposure of the ileum to nutrients produce weight loss and improved glycaemic control. Third, the appetite-reducing effect of chronic ileal brake activation appears to be maintained over time. Together, this evidence suggests that activation of the ileal brake is an excellent long-term target to achieve sustainable reductions in food intake.

Schellekens et al. and Varum et al. both successfully designed systems for targeted and site-specific drug delivery in the GI tract (Schellekens R C A, Stellaard F, Olsder G G, Woerdenbag H J, Frijlink H W, Kosterink J G W. Oral ileo-colonic drug delivery by the colopulse-system: A bioavailability study in healthy volunteers. J Control Release. 2010; 146(3):334-40. Varum F J, Hatton G B, Freire A C, Basit A W. A novel coating concept for ileo-colonic drug targeting: proof of concept in humans using scintigraphy. Eur J Pharm Biopharm. 2013; 84(3):573-7). Previous studies have employed an oil emulsion product (Fabuless®, Olibra®) aiming at more distal delivery of fat. These products were based on specific physico-chemical properties of an emulsifier (Burns A A, Livingstone M B, Welch R W, Dunne A, Rowland I R. Dose-response effects of a novel fat emulsion (Olibra) on energy and macronutrient intakes up to 36 h post-consumption. Eur J Clin Nutr. 2002; 56(4):368-77. Burns A A, Livingstone M B, Welch R W, Dunne A, Robson P J, Lindmark L, et al. Short-term effects of yoghurt containing a novel fat emulsion on energy and macronutrient intakes in non-obese subjects. Int J Obes Relat Metab Disord. 2000; 24(11):1419-25. Burns A A, Livingstone M B, Welch R W, Dunne A, Reid C A, Rowland I R. The effects of yoghurt containing a novel fat emulsion on energy and macronutrient intakes in non-overweight, overweight and obese subjects. Int J Obes Relat Metab Disord. 2001; 25(10):1487-96). Fabuless was shown to decrease food intake and increase satiety in studies by Burns et al, although this was not confirmed by others (Diepvens K, Steijns J, Zuurendonk P, Westerterp-Plantenga M S. Short-term effects of a novel fat emulsion on appetite and food intake. Physiol Behay. 2008; 95(1-2):114-7. Logan C M, McCaffrey T A, Wallace J M, Robson P J, Welch R W, Dunne A, et al. Investigation of the medium-term effects of Olibratrade mark fat emulsion on food intake in non-obese subjects. Eur J Clin Nutr. 2006; 60(9):1081-91. Chan Y K, Strik C M, Budgett S C, McGill A T, Proctor J, Poppitt S D. The emulsified lipid Fabuless (Olibra) does not decrease food intake but suppresses appetite when consumed with yoghurt but not alone or with solid foods: a food effect study. Physiol Behay. 2012; 105(3):742-8. Smit H J, Keenan E, Kovacs E M, Wiseman S A, Peters H P, Mela D J, et al. No efficacy of processed Fabuless (Olibra) in suppressing appetite or food intake. Eur J Clin Nutr. 2011; 65(1):81-6). It was hypothesized that food processing may have diminished the ability of Fabuless to deliver undigested fat to the distal small intestine.

WO2013/063527 discloses oral dosage forms comprising hormone releasing substances contained within an enteric coating configured to release the contents in the ileum. The coating employs an excipient selected from various expensive pharmaceutical excipients such as ethyl cellulose, hydroxypropylmethyl cellulose and polyvinyl acetate phthalate. Various hormone releasing substances are disclosed including sugars, polypeptides, free fatty acids, amino acids and lipids.

It is an object of the invention to overcome at least one of the above-referenced problems.

SUMMARY OF THE INVENTION

The applicant provides microparticles having a lipid payload contained within a tightly-knit protein carrier for the purpose of oral delivery of lipid intact to the ileum for the purpose of stimulating the ileal brake and attenuating appetite in healthy and obese individuals. The tightly-knit protein carrier may be a polymerised protein membrane surrounding a lipid core (mononuclear), or it may be a polymerised protein matrix containing droplets of lipid dispersed though the matrix (multinuclear). The tightly-knit protein carrier is generated from denatured or hydrolysed protein, typically dairy or plant protein, that is crosslinked during the production process to provide a non-permeable membrane or matrix. This stabilises the lipid within the carrier, and in addition obviates the need for the lipid to be emulsified, thereby increasing the lipid payload of each microparticle which in turn allows more lipid to be delivered per gram of delivery vehicle. In addition, the use of plant or dairy protein avoids the need to use expensive pharmaceutical excipients, and allows for the provision of a food ingredient powder (i.e. microparticle powder) that contains stabilised lipid, that may be used as required to produce unit dose oral dosage forms for use in attenuation of appetite. Applicant has also discovered that delivery of lipid to the ileum of a subject in a micro-encapsulated form generated a greater gut peptide hormone response, principally with Peptide YY (PYY)

response and promotes satiety and attenuates hunger pangs in the subject. Lipid containing microcapsules which release their macronutrient content in the distal bowel, rather than the stomach, induce a higher PYY response, lowers food intake and promotes the feeling of hunger. The Applicant has shown that when the micro-encapsulated lipid is administered to a subject before a meal (for example 2-3 hours before a meal), the subject's appetite is reduced just prior to the meal and the subject consumes less food during the meal. The micro-encapsulated lipid may therefore be used to regulate food intake in subjects, both in a therapeutic and non-therapeutic context.

According to a first aspect of the present invention, there is provided a method of inducing satiety in a mammal, the method comprising orally administering a composition to the mammal, in which the composition comprises microparticles comprising lipid contained within a gastric-resistant, ileal-sensitive, non-porous carrier configured for release of the lipid in the distal ileum.

According to another aspect of the present invention, there is provided a method of regulating food intake in a mammal, the method comprising orally administering a composition to the mammal, in which the composition comprises microparticles comprising lipid contained within a gastric-resistant, ileal-sensitive, non-porous carrier configured for release of the lipid in the distal ileum.

According to a further aspect of the invention, there is provided a method of treating or preventing obesity in a mammal, the method comprising orally administering a composition to the mammal, in which the composition comprises microparticles comprising lipid contained within a gastric-resistant, ileal-sensitive, non-porous carrier configured for release of the lipid in the distal ileum.

The Applicant has also discovered that consumption of certain levels of micro-encapsulated lipid relieves constipation by precipitating bowel movements shortly after consumption. The dose required to achieve this effect is generally greater than 400 Kcal encapsulated lipid, for example 400-600 kCal encapsulated lipid.

According to a further aspect of the invention, there is provided a method of treating or preventing constipation in a mammal, the method comprising orally administering a composition to the mammal, in which the composition comprises microparticles comprising lipid contained within a gastric-resistant, ileal-sensitive, non-porous carrier configured for release of the lipid in the distal ileum.

The composition may be a food, beverage, food supplement, food ingredient, or pharmaceutical product. In one embodiment, the composition is a powder.

The microparticles may have a mononuclear morphology, with a lipid core encapsulated within a polymerised shell formed from, for example, polymerised protein. The microparticles may also have a multinuclear morphology in which the carrier is a matrix (for example a polymerised protein matrix) in which lipid is dispersed throughout the matrix.

In one embodiment, the microparticles comprise a core and a shell encapsulating the core, in which the core comprises or consists of lipid (i.e. mononuclear).

In one embodiment, the core consists essentially of lipid. In other embodiments, the core comprises additional components, for example nutritional components, for example lipids/oils, plant seed oils, essential oils from an alternative source, carbohydrate, protein, vitamins or minerals, or a combination thereof.

In one embodiment, at least 65%, 70%, 75%, 80%, 85%, 90%, 95% by weight of the microparticle is lipid.

In another embodiment, the microparticles comprise a carrier matrix with lipid dispersed throughout the matrix (i.e. multinuclear).

In one embodiment, the lipid is in a solid form.

In one embodiment, the microparticles are formed by fluidised bed drying.

In one embodiment, the lipid is in in liquid form.

In one embodiment, the microparticles are microencapsulates formed by micronozzle extrusion, and preferably micronozzle co-extrusion.

In one embodiment, all or substantially all of the lipid (i.e. at least 90% of the lipid) in the composition is contained within the gastric-resistant, ileal-sensitive, non-porous carrier configured for release of the lipid in the distal ileum, with enhance stability against primary and secondary oxidation.

In one embodiment (satiety, food intake regulation, gut peptide hormones, obesity treatment), the composition is provided in a unit dose form, in which the composition comprises 50 to 400, 100-350, 100-300, 150-300 Kcal of lipid. The unit dose form may be a capsule or a tablet, or a beverage, or a sachet of powder to be mixed with liquid, or a snack of other food product, containing the defined amount of microencapsulated lipid, or combination of lipids.

In another embodiment (constipation), the composition is provided in a unit dose form, in which the composition comprises 400-1000, 400-700, 400-600, 400-550 Kcal of lipid. The unit dose form may be a micro-capsule, microparticulate, capsule or a tablet, or a beverage, or a snack of other food product, containing the defined amount of lipid.

In one embodiment, the lipid is an unsaturated lipid, ideally a polyunsaturated lipid. In one embodiment, the lipid is derived from a vegetable, algae, marine, plant or plant seed oil, egg and nuts.

In one embodiment, the lipid is a mixture of unsaturated lipids, ideally a polyunsaturated lipid. In one embodiment, the lipids are derived from a vegetable, algae or plant source and no emulsifier is needed for the formulation.

In one embodiment, at least 90% of the lipid in the composition is contained within a gastric-resistant, ileal-sensitive, carrier configured for release of the lipid in the distal ileum (i.e. is provided by the microparticles). Thus, for example, when the composition is a food product such as a health bar which contained the micro-encapsulated lipid, the bar may also contain some lipid in non-encapsulated form.

In one embodiment, the carrier comprises or consists of protein. In one embodiment, the protein is denatured or hydrolysed protein. In one embodiment, the protein is dairy or plant or vegetable protein.

In one embodiment, the composition is a food ingredient powder. In one embodiment, the food ingredient powder is formed by micro-nozzle co-extrusion or fluidised bed drying.

In one embodiment, the composition is a food ingredient powder. In one embodiment, the food ingredient powder is formed by micro-nozzle co-extrusion or fluidised bed drying with enhance stability against primary and secondary oxidation.

In one embodiment, the composition is a food or beverage product.

In one embodiment, the use is inducing satiety in a subject with weight management problems for example an overweight or obese person.

In one embodiment, the composition is administered before a meal, for example 1-3 hours before a meal.

In one embodiment, the use is generating a stable high concentrated lipid-containing, with a prolonged shelf-life and oxidative stability that is capable of inducing satiety, In one embodiment, the use is generating a stable high concentrated lipid-containing, with a prolonged shelf-life and oxidative stability, that is capable of relieving constipation without additional pharmaceutical excipients.

In another aspect, the invention provides a composition of microparticles, in which the microparticles comprise lipid contained within a gastric-resistant, ileal-sensitive, carrier configured for release of the lipid in the ileum, and in which the shell preferably comprises a polymerised plant or dairy protein membrane.

The microparticles may have a mononuclear morphology, with a lipid core encapsulated within a polymerised shell formed from, for example, polymerised protein. The microparticles may also have a multinuclear morphology in which the carrier is a matrix (for example a polymerised protein matrix) in which lipid is dispersed throughout the matrix.

In one embodiment, the carrier comprises or consists of protein. In one embodiment, the protein is denatured or hydrolysed protein. In one embodiment, the protein is dairy or plant or vegetable protein.

In one embodiment, the composition comprises 100-400 Kcal of lipid, in which the lipid is contained within the microparticles.

In one embodiment, the lipid core consists essentially of lipid.

In one embodiment of the mononuclear microcapsule, the lipid in the multinuclear lipid core is not emulsified.

In one embodiment, the plant or dairy protein is denatured or hydrolysed plant or dairy protein, and the lipid core consists essentially of lipid.

In one embodiment, the plant or dairy protein is denatured or hydrolysed plant or dairy protein, and the composition comprises 100-400 Kcal of lipid, in which the lipid is contained within the microparticles.

In one embodiment, the plant or dairy protein is denatured or hydrolysed plant or dairy protein, the lipid core consists essentially of lipid, and the composition comprises 100-400 Kcal of lipid, in which the lipid is contained within the microparticles.

In one embodiment, the microparticles are produced by fluidised bed drying or via atomization of liquid particles at elevated temperatures.

In one embodiment, the microparticles are produced by micro-nozzle extrusion, especially micro-nozzle co-extrusion.

In one embodiment, the microparticles have an average dimension of less than 500 microns as determined by laser diffractometry.

In one embodiment, the microparticles have an average dimension of less than 200 microns as determined by laser diffractometry.

In one embodiment, the composition is a unit dose composition (for example, a capsule or tablet, or sachet).

In one embodiment, the microparticles are dried.

In another aspect, the invention provides a method of producing a composition of microparticles comprising a lipid core contained within a gastric-resistant, ileal-sensitive, shell configured for release of the lipid in the ileum, and in which the shell preferably comprises a polymerised plant or dairy protein membrane.

In one embodiment, the method a dual concentric nozzle extruder having an inner nozzle and an outer nozzle concentrically arranged around the inner nozzle, the method comprising the steps of simultaneously extruding lipid through the inner nozzle and a denatured or hydrolysed protein dispersion through the outer nozzle for form microdroplets, and polymerising the microdroplets in a polymerisation bath to form microparticles, and optionally drying the microparticles.

In another embodiment, the method comprising the steps of providing:

solid lipid microparticles on a fluidised bed, spraying a protein solution (i.e. 5-15% w/v) onto the bed to coat the lipid particles and form microparticles, and drying the microparticles.

In one embodiment, a second protein solution (5-15% w/v) is sprayed on to the dried microparticles. In one embodiment, the second protein solution comprises protein in a weakly acidic buffer.

In one embodiment, the method of making the microparticles comprises treating a liquid formulation by atomization via extrusion at elevated pressure through a nozzle under elevated temperature conditions to generate microcapsules comprising essentially a lipid core.

Other aspects and preferred embodiments of the invention are defined and described in the other claims set out below.

BRIEF DESCRIPTION OF THE FIGURES

FIG. 2: Timeline of the test day. A test drink (micro-encapsulated fat for targeted delivery to the distal ileum or control drink—fat for targeted delivery to the stomach) was ingested in a fasted state. Body measurements, blood samples and VAS scores were collected at several time points as indicated in FIG. 1 during Trial 1 and Trial 2.

Figure 3:
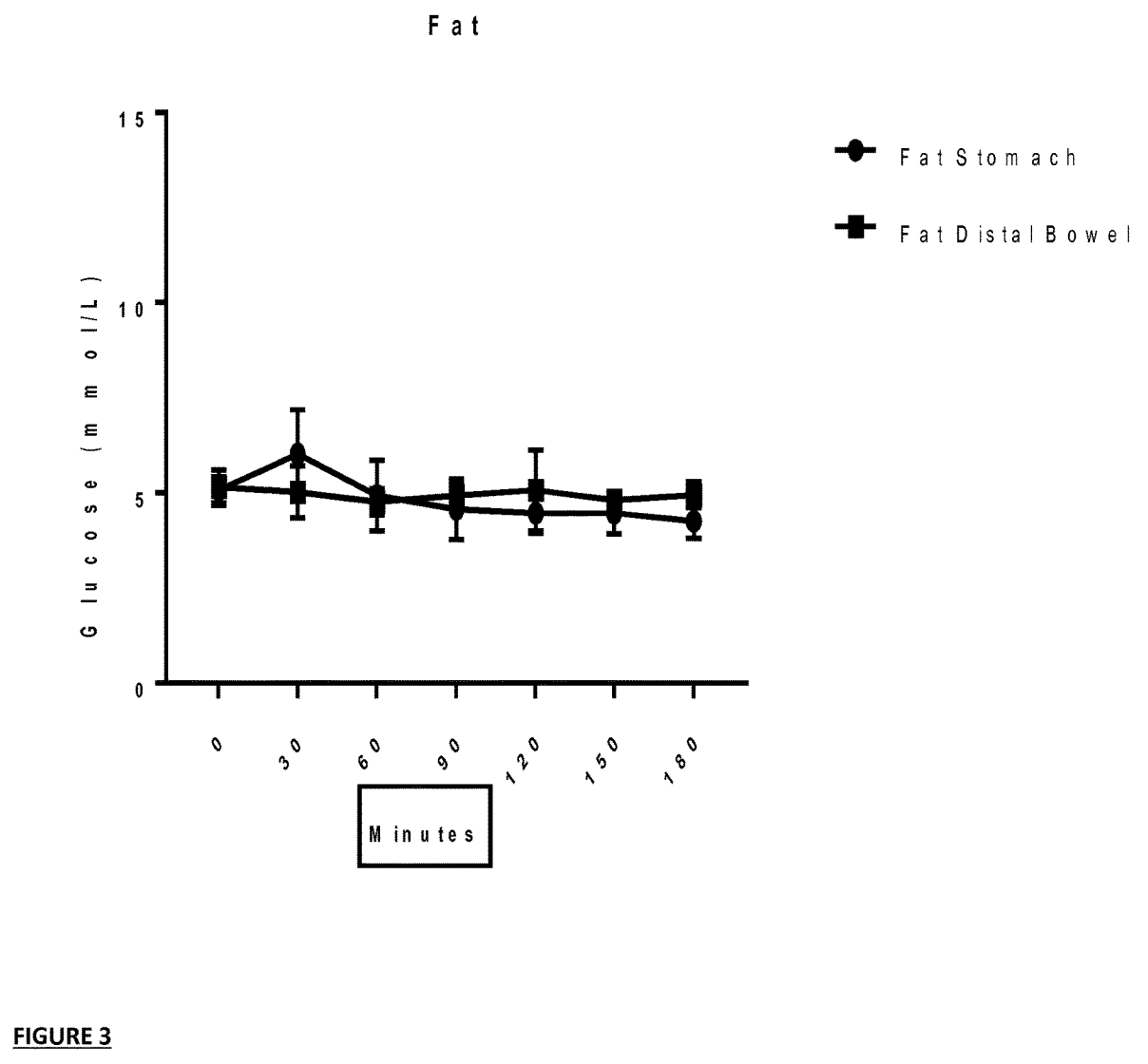

FIG. 3. Total glucose response before and after ingestion of the micro-encapsulated test drink (micro-encapsulated fat for targeted delivery to the distal ileum or control drink (fat for targeted delivery to the stomach). Ingestion took place after overnight fasting.

DETAILED DESCRIPTION OF THE INVENTION

Figure 1:
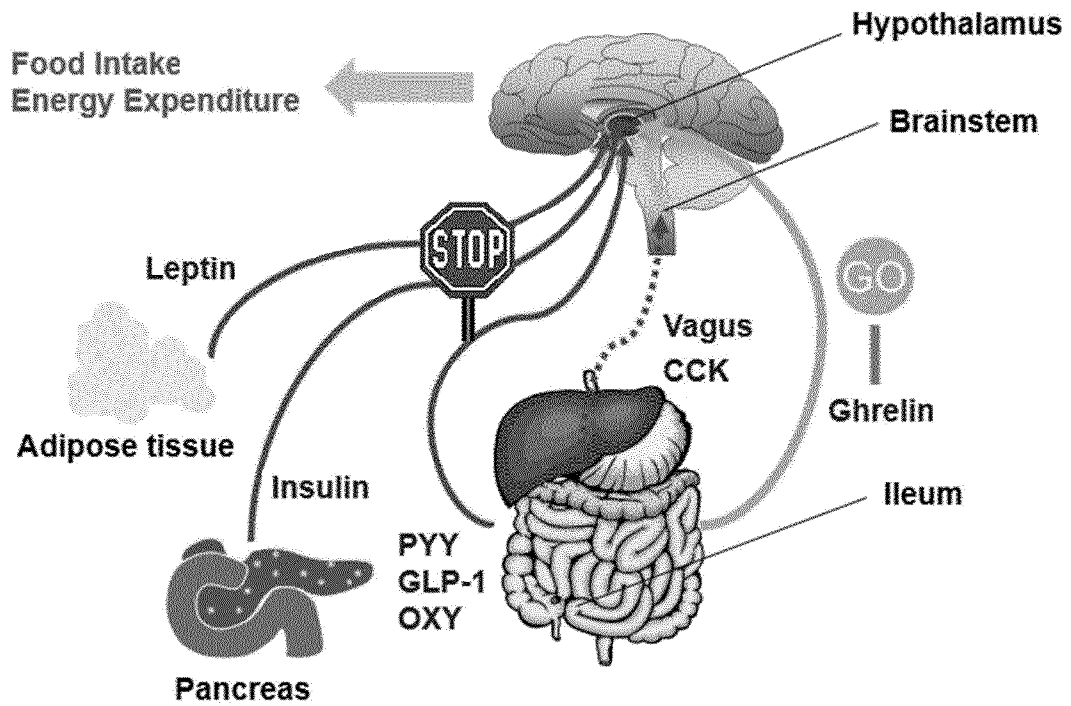
FIG. 1. Schematic illustrating appetite regulation—source: Vincent, le Roux et al., Nature Clin Practice Gastro & Hepatology 2008

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "obesity" as applied to a mammal means a body mass index of greater than 30 $Kg/m^2$. The term includes Class I obesity (BMI 30-35), Class II obesity (BMI 35-40), Class III obesity (BMI>40), morbid obesity (BMI of ≥35 kg/m2 and experiencing obesity-related health conditions or ≥40-44.9 kg/m2) and super obesity (BMI of ≥45 or 50 kg/m2). Obesity may be caused by a number of different factors, including excessive eating, lack of physical activity, or genetic susceptibility.

As used herein, the term "overweight" as applied to a mammal refers to a mammal having a BMI of 20-30 $Kg/m^2$.

As used herein, the term “regulating food intake” as applied to a mammal means reducing the food intake compared with mammal who is not subject to the method or use of the invention.

As used herein, the term “constipation” as applied to a mammal refers to a condition where the mammal has bowel movements that are infrequent or hard to pass. Other symptoms include bloating and abdominal pain. Constipation may be caused by inflammatory bowel disease, diabetes, hyperthyroidism, Parkinson’s disease, celiac disease, colon or bowel cancer. Treatment of constipation includes partial or complete treatment of the constipation or its symptoms. Prevention of constipation includes preventing the occurrence, for example in patients with colon cancer who may take the composition as a prophylactic measure or to prevent the condition worsening.

As used herein, the term “inducing satiety” as applied to a mammal means inducing a feeling of partial or complete fullness in the mammal and/or less pronounced hunger feelings. (Vincent, le Roux et al. Nature Clin Practice Gastro & Hepatology 2008). Levels of peptide YY (PYY), a key satiety gut hormone, are diminished in the obese population (FIG. 1). The density of endocrine L cells, which release PYY, is higher in the distal GIT than in the proximal GIT. Satiety gut hormones such as cholecystokinin (CCK), glucagon-like peptide 1 (GLP-1) and peptide YY (PYY) play a role in the homeostatic regulation of food intake, by signalling to hypothalamic nuclei like the ARC. Changes in circulating levels of many of these hormones occur after weight loss Thus, the method of the invention may comprise administering the composition prior to a meal with the view of inducing satiety prior to the meal and consequently consuming less food during the meal (i.e. regulating food intake). The composition may be administered between meals, for example 1-3 hours before a meal, or it may be administered with a meal. In one embodiment, the composition is administered at least once a day, for example 2, 3 or 4 times a day. In one embodiment, the composition comprises 100-400 Kcal of lipid.

As used herein, the term “composition” refers to a composition suitable for oral administration and includes foods, beverages, food supplements, food ingredients (for example powders comprising microparticulates) and pharmaceutical compositions. The composition comprises or consists of high GI carbohydrate contained within a gastric-resistant, and ileal-sensitive, dry non-porous shell. In one embodiment, the composition comprises or consists of a microparticulate.

As used herein, the term “Lipid” includes triglycerides, monoglycerides, diglycerides, phospholipids, fatty acids (essential or non-essential), or compositions enriched in such lipids such as fish oils, omega-3 oils, or omega-6 oils, krill oil, algal oil, seed oils, purified fatty acid compositions (for example purified LC-PUFA’s, DHA or ARA) and which may contain phospholipids, antioxidants and other fat-soluble components such as fat-soluble vitamins. In one embodiment, the lipid is a purified fatty acid. “Fatty acids” are classified based on the length and saturation characteristics of the carbon chain. Fatty acids include fatty acids in various forms, including but not limited to triacylglycerols, diacylglycerols, monoacylglycerols, phospholipids, free fatty acids, esterified fatty acids, and natural or synthetic derivative forms of these fatty acids (e.g. calcium salts of fatty acids, ethyl esters, etc). Short chain fatty acids have 2 to about 7 carbons and are typically saturated. Medium chain fatty acids have from about 8 to about 17 carbons and may be saturated or unsaturated. Long chain fatty acids have from 18 to 24 or more carbons and may also be saturated or unsaturated. In longer chained fatty acids there may be one or more points of unsaturation, giving rise to the terms “monounsaturated” and “polyunsaturated,” respectively. The lipid may be derived from any source, for example fish, algae, krill, animals, vegetables, egg, nuts and seeds.

In one embodiment, the lipid is a PUFA, preferably a long-chain PUFA (LC-PUFA). “LC-PUFAs” are categorized according to the number and position of double bonds in the fatty acids according to a well understood nomenclature. There are two common series or families of LC-PUFAs, depending on the position of the double bond closest to the methyl end of the fatty acid: the n-3 (or ω-3 or omega-3) series contains a double bond at the third carbon, while the n-6 (or ω-6 or omega-6) series has no double bond until the sixth carbon. Examples of LC-PUFA’s include DHA and EPA. “Docosahexaenoic acid” (“DHA”) refers a fatty acid with a chain length of 22 carbons with 6 double bonds beginning with the third carbon from the methyl end and is designated “22:6 n-3”. “Eicosapentaenoic acid” (“EPA”) which is designated “20:5 n-3” and docosapentaenoic acid n-3 (“DPA(n-3)”) which is designated “22:5 n-3.” “Arachidonic acid” (“ARA”) which is designated “20:4 n-6” and docosapentaenoic acid n-6 (“DPAn-6”) which is designated “22:5 n-6” are suitable.

As used herein, the term “microparticle” or “microparticulate” refers to particulates having an average dimension of less than 1000 microns that contains lipid protected from gastric release by a non-porous cartier configured for ileal release. The microparticles may have a mononuclear or multinuclear morphology. The microparticulates may be formed by a number of different methods, including fluidised bed drying methods and micro-nozzle extrusion or co-extrusion methods. Micro-nozzle extrusion methods are described in the literature, and generally employ extrusion of beads through a suitable extruder and then solidification of the beads in a suitable bath, for example a bath containing an acidic buffer or a ascorbate buffer. A single nozzle system may be employed, where the lipid and shell forming material (i.e. denatured protein) are provided as a single suspension which is extruded through an extruder to form microdroplets which are solidified in a solidification bath, and then dried (multinuclear morphology). Such microparticulates generally have a solid matrix of, e.g. denatured or polymerised protein, and pockets of lipid dispersed throughout the matrix. Alternatively, a double nozzle system may be employed in which a lipid is extruded from a central nozzle, and the shell forming material may be extruded through an outer, concentric, nozzle, forming droplets having a lipid core encapsulated within an outer shell (micronozzle co-extrusion). The microdroplets are then solidified within a gelling bath and no emulsifier is generally required i.e. lecithin. Extrusion methods of forming microparticulates are described in WO2010/119041, WO2014/198787, WP2016/096929, WO2016/178202, and WO2016/185053. Generally, the methods are referred to herein as “extrusion methods” or “micro-nozzle extrusion methods” and the resultant micr-particulates are referred to herein as “microencapsulates”. The microparticulates may also be formed by other, non-nozzle extrusion methods, for example by means of spray coating in a fluidised bed system (aka fluidised bed drying) described below, the details of which will be known to a person skilled in the art and described in the literature, examples can be found in the following literature: Anal, A., et al., 2007. Recent advances in microencapsulation of probiotics for industrial applications and targeted delivery. Trends in food Science and Technology, Volume 18, Issue 5, pg 240-251) (Nazzaro, F., et al., 2012. Microencapsulation in food science and biotechnology, Current Opinion in Biotechnology, Volume 23, Issue 2, 2012, pg182-186). In these embodiments, each microparticulate may comprise an agglomerate of small microparticulates, and the core is generally solid. An essential part of the process employed to produce the microparticulate is that the core is protected by a carrier (coating) that is gastric resistant and capable of ileal release. In the embodiments described below, the Applicant has employed heat-treated or hydrolysed protein for this purpose (for example, denatured or hydrolysed milk, casein or whey protein), although other carrier materials may be employed that are suitable for gastric protection and ileal release. In a preferred embodiment of the invention, the carrier is a protein material, especially a milk or plant protein. In one embodiment, the microparticles or microcapsules are dried.

As used herein, the term "gastric-resistant" as applied to the composition (or the microparticulate contained within the composition) means that the composition or microparticulate can survive intact for at least 60 minutes in the simulated stomach digestion model described in Minekus et al., 1999 and 2014 (A computer-controlled system to simulate conditions of the large intestine with peristaltic mixing, water absorption and absorption of fermentation product, Minekus, M., Smeets-Peeters M, Bernalier A, Marol-Bonnin S, Havenaar R, Marteau P, Alric M, Fonty G, Huis in't Veld J H, Applied Microbiology Biotechnology. 1999 December; 53 (1):108-14) and (Minekus et al., 2014, A standardised static in vitro digestion method suitable for food—an international consensus, Minekus, A. et al., Food Function, 2014, 5, 1113).

As used herein, the term "ileal-sensitive" as applied to the composition (or the microparticulate contained within the composition) means that the composition or microparticulate are capable of releasing their contents in vivo in the ileum of a mammal.

As used herein, the term "coating material" or "carrier material" refers to material that is GRAS status and is capable of forming a shell or coating around lipid and is gastric-resistant and capable of ileal release. In a preferred embodiment, the coating material is protein, preferably a diary or vegetable protein. The protein is generally denatured or hydrolysed. In one embodiment, the dairy protein is selected from milk protein concentrate, whey protein concentrate, whey protein isolate, and a caseinate, for example calcium or sodium caseinate. The vegetable protein may be a protein derived from pea, egg, wheat or rice, or any combination thereof. The protein may be in the form of a concentrate or an isolate. In one embodiment, the coating material may be an enteric coating material commonly employed in the pharmaceutical industry; examples include methyl-(meth)acrylate-methacrylic acid copolymers, cellulose acetate phthalate, cellulose acetate succinate, sodium alginate, and shellac.

As used herein, the term "denatured" as applied to protein refers to means partially or fully denatured. Preferably at least 90%, 95% or 99% of the protein is denatured. A method of determining the % of denatured protein is provided below.

As used herein, the term "polymerised" as applied to protein refers to as applied to the protein of the membrane shell means that the protein is crosslinked, for example as a result of cold-gelation in a gelling bath or by drying on a fluidised bed dryer. Preferably, the polymerized protein forms a water, air, or water and air impermeable shell.

As used herein, the term "hydrolysed" as applied to a protein means that the protein has been treated to at least partially digest native protein, in one embodiment treated with a protease enzyme composition. Suitably, the hydrolysed protein has a degree of hydrolysis (% DH) of 18-85%. Degree of hydrolysis (DH) is defined as the proportion of cleaved peptide bonds in a protein hydrolysate, and is determined using the OPA spectrophotometric assay, which involve the using N-acetyl-L-Cysteine (NAC) as the thiol reagent.

As used herein, the term "distal ileum" or "distal bowel" refers to the part of the ileum small intestine that intersects with the large intestine. It contains the ileocecal sphincter, a smooth muscle sphincter that controls the flow of chyme into the large intestine. The distal ileum is the distal segment of small bowel. It immediately precedes the small bowel's connection with the colon through the ileo-caecal valve. While the small intestine is well characterised for its roles in the digestion and absorption of nutrients, it mediates another important role in its ability to sense the presence of nutrients in the gut lumen. This area of the intestine is of interest since the distal bowel has a higher density of L-cells and therefore a potentially greater PYY response, which may result in enhanced postprandial satiety and reduced food intake.

As used herein, the term "unit dose" or "dose" as applied to a composition for weight management or obesity refers to an amount of the composition that contains 10-400 Kcal of lipid contained within a gastric-resistant coat. The (unit) dose may be a beverage or a food product, or a tablet. As used herein, the term "unit dose" or "dose" as applied to a composition for relief of constipation refers to an amount of the composition that contains more than 400 Kcal of protected lipid, for example 400-600 Kcal of lipid contained within a gastric-resistant coat. The (unit) dose may be a beverage or a food product, or a tablet.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Example 1

Materials and Methods

The study was approved by the Medical Ethics Committee and was conducted in full accordance with the principles of the Declaration of Helsinki of 1975 as amended in 2013, and approval from the Irish and European Medical Research Committee. All participants gave written informed consent before participation. This trial was registered at www.cparticlinicaltrials.gov as required.

Participants

Two studies were performed as per the details below. Power analysis was performed, eight healthy volunteers were recruited for the first study and 72 healthy volunteers recruited for the second study. Volunteers were recruited by local advertisements and posters outlining the study initiative were placed in public areas such as hospital waiting rooms, with contact information. Social media websites such as Twitter were also used to advertise. Advertisements only contained essential information relating to the study and contact details as approved by the ethics committee. Potential participants identified through these methods were thus able to contact the study lead manager, after which they received written information providing further details about the study and were invited to attend a screening visit.

Screening

Screening visits took place at the Clinical Research Centre. Volunteers were fully informed on what the study entailed and any risks involved in participating. They were made aware that they reserved the right to withdraw at any given time during the study and that their data would not be used if they did so. Participants were given the Participant Information Sheet to read and had the opportunity to raise any questions or concerns. Written informed consent was obtained after an interval of at least 14 days.

It was necessary to exclude individuals with metabolic dysfunction or any other condition or comorbidity that may have compromised compliance rates and ability to participate, such as diabetes, obesity, smoking, substance abuse, pregnancy, use of medications, and chronic illness. All participants reported a stable weight 1 month before screening were not involved in any diet in the 12 months previous to the study.

At this point, if the participant was satisfied to proceed, consent was obtained and their eligibility was further assessed according to the inclusion and exclusion criteria. Inclusion criteria for both trials included age 18-50 years, normal fasting glucose and source, a body mass index (BMI) between 25 and 30 kg/m$^2$.

Based on the power calculation, two studies were completed; one with 8 participants and a second study with 72 participants based on a randomised, double-blinded, crossover study (consideration was given to previous clinical trials performed in the area and expected number of dropouts).

Study Design

This double-blind, randomized, controlled crossover study compared the effect of a micro-encapsulated fat compound targeting the distal bowel with that of an identical control product (fat with alginate encapsulation which disintegrates in the stomach). The study product was ingested in a fasted state, to allow the stomach and GI tract to be void any influential factors or gastric emptying effects. For this reason, no breakfast was provided to avoid complications with data interpretation. Each of the subjects were randomised to receive the micro-encapsulated drinks during successive visits and randomisation was based on age and gender in randomized block designs: Test days were scheduled with a wash out period of 1.5 weeks in between to avoid complex effects.

Study Products

The lipid micro-particulates/microencapsulated were designed for release in the distal bowel were generate using one of two methods:

METHOD 1: Co-extrusion production of powdered lipid micro-capsules

METHOD 2: Fluidised bed production of powder lipid micro-particulates

Option 1: Generation of Micro-Capsules

The micro-encapsulation system entraps lipid to generate micron-sized micro-capsules for controlled delivery of lipids to the distal bowel. Lipids micro-capsules were produced according to GMP guidelines (Bleiel S, inventor Gastro-resistant microencapsulates, and uses thereof to stimulate in-vivo ileal GLP-1 release in mammal. Ireland 2016 23 Jun. 2016 and WO2016/193373). A highly concentrated oil was co-extruded through a micron-concentric nozzle apparatus. The outer nozzle containing denatured whey protein was concentrically arranged around an inner nozzle containing the fat/lipid load. This enables the extrusion of the denatured whey protein through the outer nozzle and fat was co-extruded in the inner nozzle. Flow rates were managed precisely to enable consistent flow of outer and inner fluids.

Generation of a Steady Jet Stream

It is important to manage efficient jet stream generation (prevent coalescence of the droplets) before the fluids reach the polymerisation bath. Hence, to prevent coalescence of the droplets, which results in loss of mono-dispersity and an increase in the standard size deviation of the resulting micro-capsules, Coulomb forces were exploited to generate a stable jet stream. The magnitude of the Coulomb force has an important effect on efficiency of encapsulation since high kV values can have a deleterious effect on carbohydrate loads and cause leakage of the core material due to enlargement of pores.

Generation of Polymerisation Buffer

An acidic buffer, was prepared as outlined in (Bleiel S, inventor Gastro-resistant microencapsulates, and uses thereof to stimulate in-vivo ileal GLP-1 release in mammal. Ireland 2016 23 Jun. 2016) or (WO2016/193373). Alternatively, an ascorbate buffer can be prepared using Na-Acetate, Ascorbic Acid. Molarity can be equilibrated at 0.4M-0.6M, pH 4.0-6.0, in order to ensure efficient encapsulation and polymerisation effects.

Micro-Capsule Production Process

The recommended micro-capsule production process temperature is 20-25° C. encapsulation of fat loads. Higher temperatures especially in combination with turbulence, can lead to increased loss of the fat inner material. Zeta potential is used to determine both attractive and repulsive features of fat and matrix protein ingredients within the micro-capsule. The magnitude of interactions will identify the optimum electrostatic potential for stable micro-capsule storage with no oxidative stress.

Method 2: Generation of Micro-Particulates

The micro-particulate system also englobs fat to generate micron-sized particulates for controlled delivery of fat to the distal bowel. Lipid microparticulates were produced according to GMP guidelines using similar solutions as outlined above i.e. Heat-treated whey protein (10% dry matter) was first admixed with an acidic buffer (PH?). This solution was then agitated at 25° C. to allow air pocket to evacuate, and then extruded through a spray micro-nozzle onto a bed of (dry) lipid particles. Once a moisture content of 8% was achieved, the coated lipid particulates would further spray with heat-treated whey protein (10% dry matter). During this second process step a weak acidic buffer, (0.25 M) such was blended with the heat-treated whey protein in order to ensure efficient encapsulation and polymerisation effects on the second coating layer. This further supports the non-porous micro-particulate coating generated. This process generates a double-coating layer of denatured whey protein on the lipid molecules. These lipid microparticulates are equally robust and protective as micro-capsules generated in METHOD 1 for the delivery of lipid to the distal bowel.

Micro-Particulate Production Process

The recommended fluidised production process temperature is 20-35° C. for encapsulation of lipid loads. Zeta potential was also used to determine both attractive and repulsive features of lipid and matrix protein ingredients within each process step i.e. first coating and secondary coating. Data again indicated a very strong protein/lipid interaction occurs at pH 4-6.5, hence an acid buffers were influential for the generation was of lipid microparticulates.

The lipid microparticulate test drink was prepared using material generated from Method 1 and Method 2. Data presented in FIGS. 1-9 illustrate a reduced gut peptide hormone response and food intake when both production methods to generate material. Hence, there is no significant difference identified in the results when material from either method 1 utilized.

Lipid microparticulates drinks were prepared using two kcal contents: 150 kcal and 500 kcal. Neither kcal loads showed any significant difference in the ad libitum food intake or gut peptide hormone responses shown in FIG. 1-9. Hence, the kcal load may not a primary influential factor for effecting hunger, satiety or gut peptide hormone responses.

The "Control test drink" was designed for lipid delivery to the stomach and it contained the same energy density (150 kcal or 500 kcal) and lipid content as the lipid microparticulate drink. Ca-alginate microbeads were prepared using GMP procedures, using 1.51% w/v sodium alginate and the crosslinking agent was calcium chloride (0.5M). The material was prepared as per the Choi et al 2007 reference (Choi, C H., et al 2007. *Generation of monodisperse alginate microbeads and in situ encapsulation of cell in microfluidic device. Biomedical devices*, Volume 9, issue 6, pg. 855-62) and the material was vacuumed dried. Residual content of calcium and chloride was tested to ensure a food-grade quality of the material.

For each study, dry powders of the carbohydrate microparticulate drink and control drink were prepared for each visit by weighing the appropriate amount to give a total calorific value of 150 kcal or 500 kcal for both carbohydrate microparticulate drinks and control drinks.

Protocol

On the day before testing, subjects were instructed to abstain from heavy exercise and consumption of alcoholic beverages and to consume the same habitual meal as per their normal diet and routine. Participants were allowed to have water and volumes were measured and recorded.

The lipid microparticulate drinks and Control drinks were prepared by an independent technician and offered to the participant in white bottles to blind both the investigator and the participant. All materials were produced according to GMP guidelines, utilising clean-label, food-grade sources of carbohydrate.

Upon arrival in the lab on both test days, an intravenous cannula was placed in a forearm vein of the participant to enable collection of blood samples.

Shoes were removed for weight and height measurements. Height was measured to the nearest 0.1 cm using a stadiometer, on the first visit only. Subjects were weighed on a digital equilibrated scale, to the nearest 0.1 kg. Waist circumference was measured in the horizontal plane to the nearest 0.5 cm using non-stretchable measuring tape.

The fasting visual analogue scale (VAS) hunger score and the baseline blood draw were taken, and the subjects then received either a 150 kcal or 500 kcal drink consisting of one of the microcapsule powder preparations diluted in water and "zero calorie" Miwadi squash flavouring.

Fasted blood samples were taken and analysis was conducted as per FIG. 2. The participant ingested the lipid microparticulate drink or the Control drink product in randomized order on different test days (T=0 min). The participant was instructed to ingest the test drink within a 10 minute time frame. At 15 min after the intake of the lipid microparticulated drink or the Control drink, subsequent blood draws were initiated.

A series of six blood samples were then taken, first at 15 min, thereafter, 5 blood draws thereafter at 30 minute intervals. One plasma sample and one serum sample were taken using the respective Vacutainer® tubes, with a total volume of 10 ml of blood drawn per timepoint (inclusive of the fasted state. All subjects were asked to rate the taste Sensory Analysis Participants were asked to complete a Questionnaire with questions related to the taste, GI symptoms were evaluated by addressing complaints such as nausea, bloating, headache, and other symptoms. Symptoms were scored on a 5-point scale with grade 0 representing 'not present' to 5 'strongly present'. GI feeling experienced from i) lipid microparticulate drink or ii) Control drink product. Success will be classified as no significant difference when participants ingested the lipid microparticulate drink or Control drink product and no stomach pain or nausea. Stimulus error was avoided in the study by giving no information to the participants relating to the content of the drink and also by providing the drinks in white bottles.

After the final blood draw, participants were offered a standardised ad libitum meal to measure their food intake. This meal was selected from a choice of four isocaloric options (chicken korma; sweet chili chicken; pasta bake; chicken tikka masala) at the beginning of the study, and the same meal was received at each visit. No technology was permitted during the meal and the participants ate in isolation to remove social influences. The subjects were instructed to eat until they felt comfortably full and to remain for 20 min irrespective of when they finished eating, after which they could go home. The amount of food consumed was quantified by weighing the food before and after consumption, and the caloric intake was subsequently calculated.

Characterization of Micro-Encapsulates

Size Distribution and Drying Effects

According to light microscopy, micro-beads demonstrated diameters of approximately 145 um with a narrow range size distribution (±4.9 μm). Laser diffractometry was also incorporated and confirmed a D (v, 0.9) values for micro-encapsulates, revealing a diameter of 278.5±1.42 μm and 145.01±4.25 μm, pre- and post-drying respectively.

Stomach Incubation and Strength of Micro-Encapsulates

Strength of micro-beads was analysed as a function of gastric incubation time in vivo (pH 1.2-1.4; 37° C.). No difference in micro-bead strength was reported for stomach incubation and enzyme-activated stomach conditions did not significantly (p, 0.001) weakened micro-bead strength. Tensile strength of micro-encapsulated remained unchanged with no reported leakage or loss of encapsulated casein, pea protein or sucrose.

Intestinal Incubation and Degradation

Micro-encapsulates were tested for intestinal delivery during in vivo transit trials. The maintenance of micro-encapsulate integrity in the duodenum 35 minutes after oral ingestion of micro-encapsulates was tested and degradation was not evident. In addition, micro-encapsulate degradation evolved according to expectations during intestinal conditions (in vivo). As time progressed, the capsulate membrane gradually degrades to release to mononuclear core material.

Plasma was separated immediately by centrifugation (3,000×g) at 4° C. for 10 min and then stored at −20° C. until analysis.

Commercially available ELISA kits (Merck KGaA, Darmstadt, Germany; Cat. #EZHPYYT66K) were used to quantify total human PYY levels. The samples were thawed for 30 minutes prior to ELISA analysis. All samples were analysed together on 96-well plates to control for variation in temperature and day-to-day error. One kit was sufficient to measure 38 unknown samples in duplicate.

This was a sandwich ELISA assay, whereby total human PYY in the sample, encompassing both PYY1-226 and PYY3-36, bound to rabbit anti-human PYY IgG to form a complex. The wells of the microtiter plate were pre-coated with anti-rabbit IgG antibodies, and the complex therefore became immobilised to the plate. A biotinylated antibody then bound to the PYY, and unbound materials were washed away. The enzyme, horseradish peroxidase, was added and conjugated to the immobilised biotinylated antibodies. Free enzyme was washed away and immobilised antibody-enzyme conjugates were quantified by measuring enzyme activity upon addition of the substrate, 3,3',5,5'-tetra-methylbenzidine.

Following acidification of the products formed, the enzyme activity was measured spectrophotometrically (CLARIOstar LABTECH), by the increased absorbance at 450 nm from the absorbance at 590 nm. Since the increase in absorbance was directly proportional to the amount of total PYY in the unknown sample, the concentration of total PYY could be derived from a standard curve generated from the standards of known PYY concentration.

Statistical Analyses

All data was tested for normality using the D'Agostino & Pearson omnibus normality test and accordingly, central tendencies were calculated and expressed using arithmetic mean±standard error of the mean (SEM). Change in subject weight over the study period was analysed using one-way repeated measures ANOVA. Three hours AUC was calculated for VAS and PYY data. VAS, PYY and food intake data were compared by release location within each macronutrient group using unpaired Student's t-tests. All analyses were two-tailed and conducted using Graphpad Prism (Windows version 6.0) software (San Diego, CA, USA). Statistical significance was set at $p<0.05$. Data are presented as the means±SEM unless specified otherwise. $P<0.05$ was considered as statistical significant. For the mixed model analysis, the significance level was set at $p<0.01$, due to multiple testing.

Results

Eight participants were included in one study and 72 participants were included in the second study. Nine participants were excluded from overall analysis, due to the inability to measure their ad libitum intake of the test meal.

In summary, micro-particulated fat delivery to the distal bowel induced a higher PYY response and subsequent reduction in food intake compared to micro-particulated fat delivered to the stomach. These differential effects were not observed when protein or carbohydrate micro-particulates were delivered to distal bowel or stomach. Activation of the ileal brake mechanism by fat may be the reason for these effects, and may represent a promising therapeutic avenue in the ongoing search for effective therapies for obesity.

Effect of Fat Delivery

Figure 4:
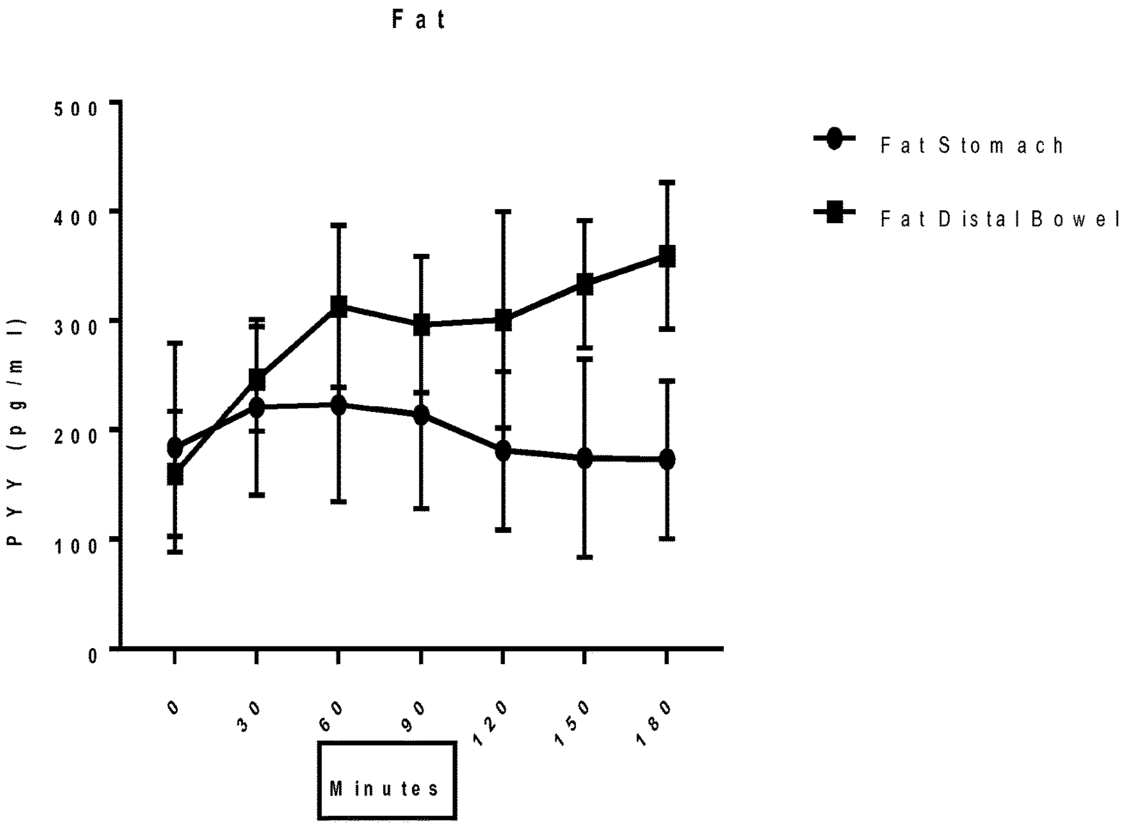
FIG. 4. Total PYY response as a function of time after ingestion of micro-encapsulated test drink. PYY data is presented before and after ingestion of the micro-particulated test drink (micro-encapsulated fat for targeted delivery to the distal ileum or control drink (fat for targeted delivery to the stomach). Ingestion took place after overnight fasting. PYY was measured in pg/mL.
Figure 5:
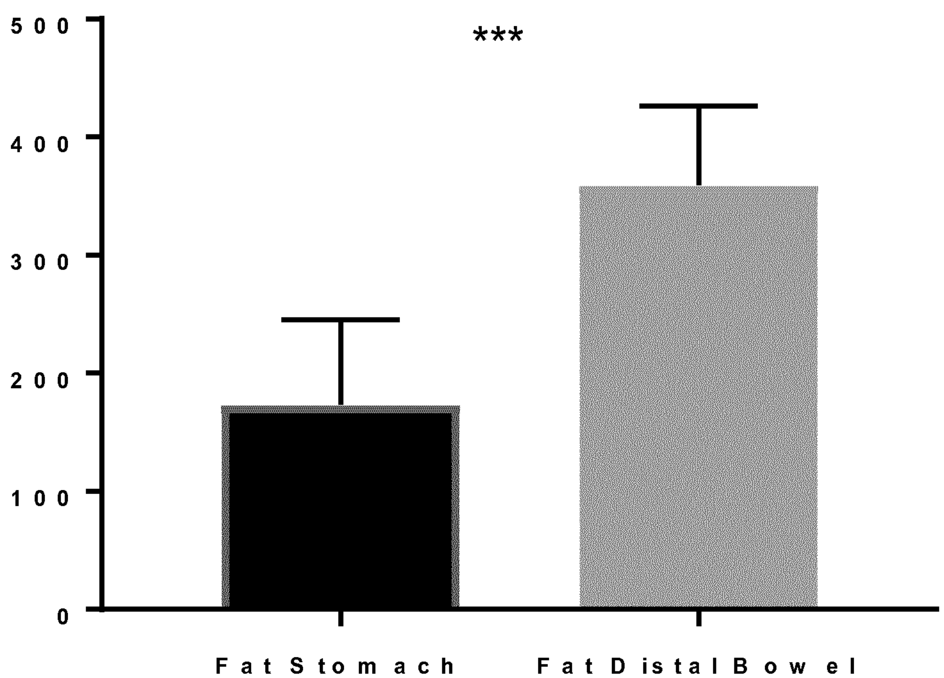
FIG. 5. Comparative PYY response as a function of delivery location (stomach vs. ileum). PYY data shown relates to the timepoint 180 min after ingestion of micro-encapsulated test drink (micro-encapsulated fat for targeted delivery to the distal ileum) and a control drink (fat for targeted delivery to the stomach). PYY was measured in pg/mL.
Figure 6:
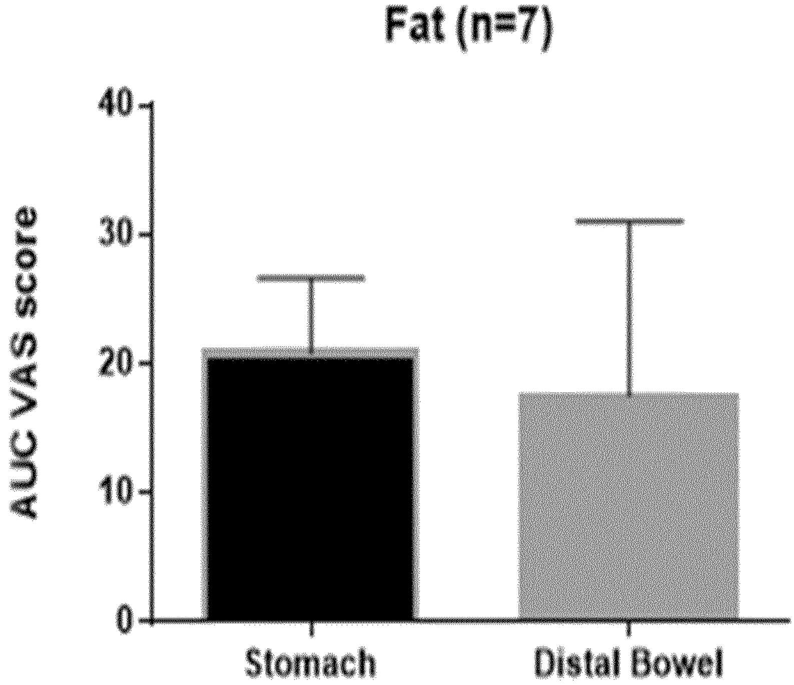
FIG. 6: Absolute VAS scores over time and AUC VAS scores for Hunger. Total AUC VAS scores 180 min after ingestion of micro-encapsulated test drink (micro-encapsulated fat for targeted delivery to the distal ileum) and a control drink (fat for targeted delivery to the stomach). Ingestion took place after overnight fasting. An ad libitum pasta meal was offered at T180 min. AUC, area under the curve; VAS, visual analogue scales. No significant difference in AUC (from 0 to 180 min) hunger (hunger: test drink vs. control, $P<0.05$) was observed.
Figure 7:
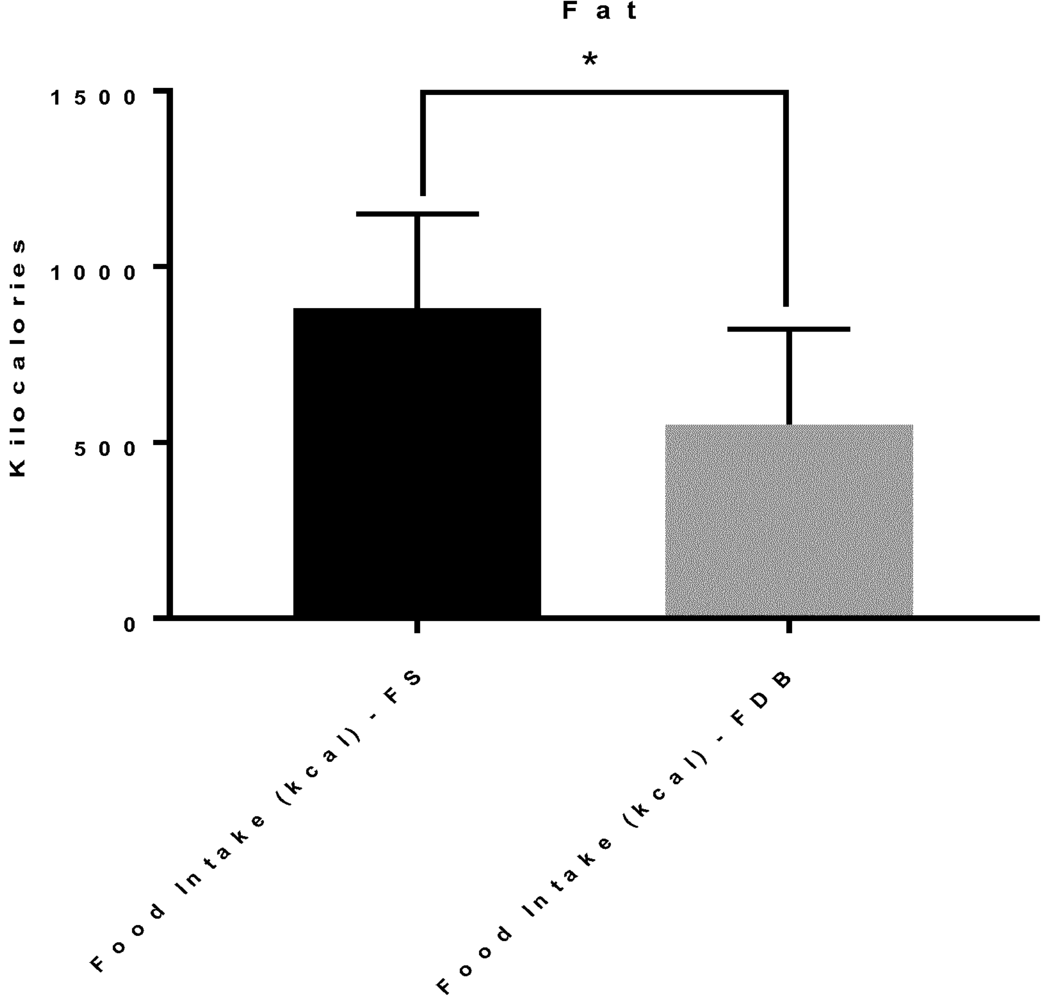
FIG. 7: Absolute VAS scores over time and AUC VAS scores for food intake. Total AUC VAS scores 180 min after ingestion of micro-encapsulated test drink (micro-encapsulated fat for targeted delivery to the distal ileum) and a control drink (fat for targeted delivery to the stomach). Ingestion took place after overnight fasting. An ad libitum pasta meal was offered at T180 min. A significant difference in AUC (from 0 to 180 min) was observed.
Figure 8:
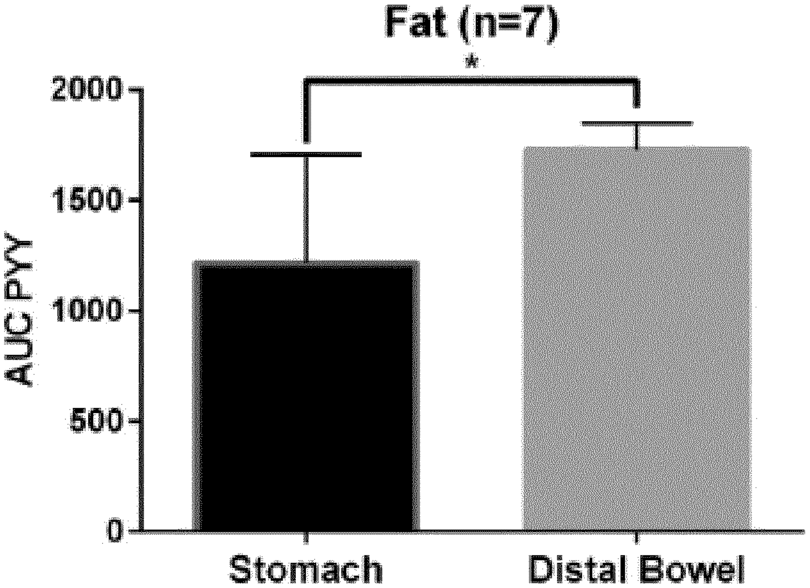
FIG. 8. Absolute AUV total PYY response as a function of time. Total PYY data min after ingestion of micro-particulated test drink (micro-encapsulated fat for targeted delivery to the distal ileum) and a control drink (fat for targeted delivery to the stomach). Ingestion took place after overnight fasting.

In this study, FIGS. 4 and 5 show that plasma PYY levels exceeded 300 pg/ml in many cases following consumption of the microparticulated fat released in the distal bowel. These supra-physiological levels, as well as the sudden and rapid increment in PYY release, likely led to the onset of these symptoms and may have functioned to suppress appetite, as opposed to increasing satiety.

Ad Libitum Food Intake

This invention demonstrated that macronutrient delivery to the distal bowel does not universally induce an increased PYY response (FIGS. 4 and 5) and reduction in ad libitum food intake (FIGS. 6 and 7), compared to the stomach. Rather, this effect is limited only to fat as outlined in FIGS. 9 and 10. While dietary fat is typically digested and absorbed in the proximal GIT, it has been shown previously that when the digestive and absorptive processes are moved to the distal GIT, the satiety gut hormone signal and quantity of food intake are affected. Ileal infusion of a lipid emulsion found that healthy subjects ate a smaller amount of food and demonstrated delayed gastric emptying compared to control infusions. The same effect was not observed with intravenous infusion of fat, implicating the ileum as the source of the effects induced by fat (Welch et al., 1985). A follow-up study by the same group compared food intake and feelings of hunger and fullness in healthy subjects receiving a lipid infusion into either the jejunum or the ileum. Both were shown to significantly reduce the quantity of food consumed compared to control, and the jejunal lipid emulsion also significantly reduced feeling of hunger prior to consumption of the meal (Welch et al., 1988).

Another study found that ileal fat perfusion was associated with slowed jejunal motility and substantial increases in plasma enteroglucagon, a GIT hormone related to GLP-1, which slows gastric motility in the distal small bowel (Spiller et al., 1984). These studies proposed the existence of a brake mechanism, which is activated by fat in the more distal parts of the GIT.

More recently, a study in healthy volunteers in which fat was delivered via a nasal tube to the duodenum, jejunum and ileum found that the ileal treatment had the most pronounced effect on food intake and satiety (Maljaars et al., 2011).

Effect of Protein Delivery

In the present study, we found that there was no differential effect exerted on PYY response and satiety between protein delivered to the stomach and distal small bowel. Indeed, there is conflicting evidence surrounding the role of protein in PYY-mediated reduction in food intake and increase in satiety. Batterham et al. showed that protein was responsible for the anorexigenic effects of PYY (Batterham et al., 2006). It was recently shown that ileal protein infusion decreased food intake compared with duodenal and control infusion, and this was associated with an increase in circulating levels of GLP-1, also released from the L-cells, compared with both jejunal and control infusion (van Avesaat et al., 2017). However, there was no effect on hunger and satiety VAS scores, nor plasma concentrations of PYY as outlined in this study in FIGS. 9 and 10.

Effect of CHO Delivery

Figure 9:
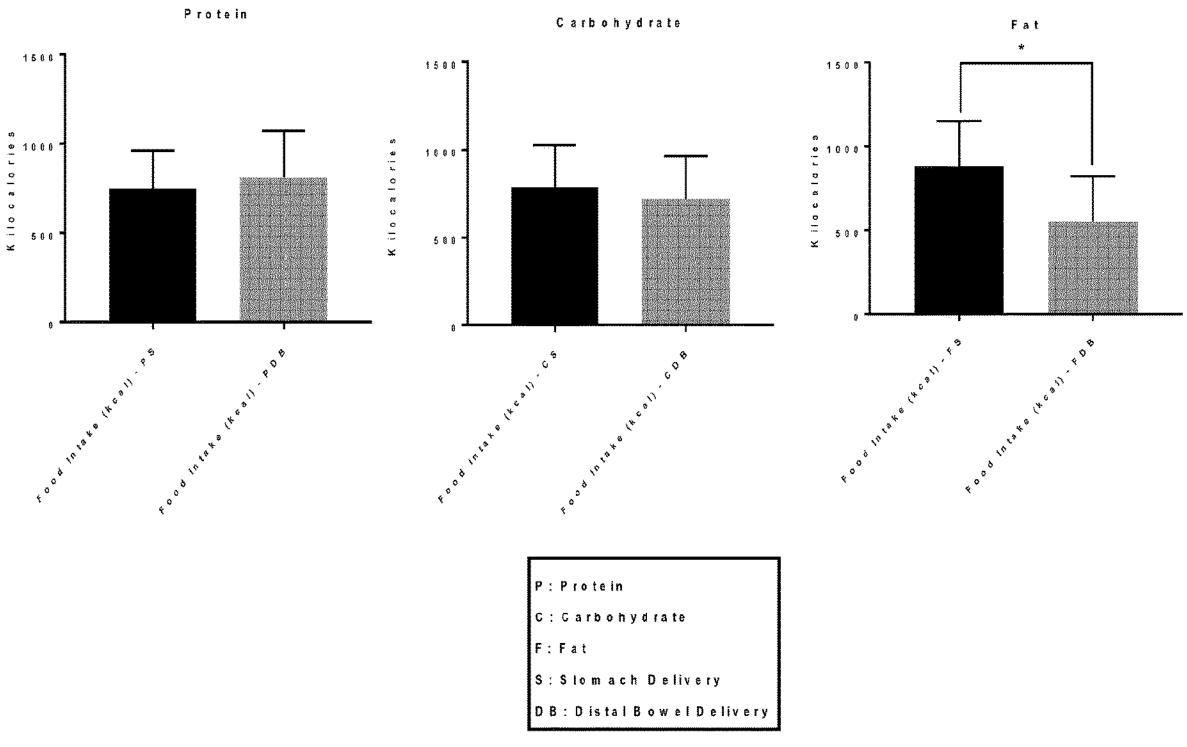
FIG. 9: Ad libitum food intake after ingestion of micro-encapsulated fat relative to other individual macronutrient following (micro-particulated test drink containing the same). Total Ad libitum food intake 180 min after ingestion of micro-particulated test drink (micro-encapsulated macro-nutrient targeted for delivery to the distal ileum) and a control drink (macronutrient for targeted delivery to the stomach). Ingestion took place after overnight fasting. Results indicate significantly ($P<0.05$) reduced food intake following distal bowel delivery of fat (FIG. 8C) compared with distal bowel delivery of protein or (FIG. 8A) and carbohydrate (FIG. 8B).
Figure 10:
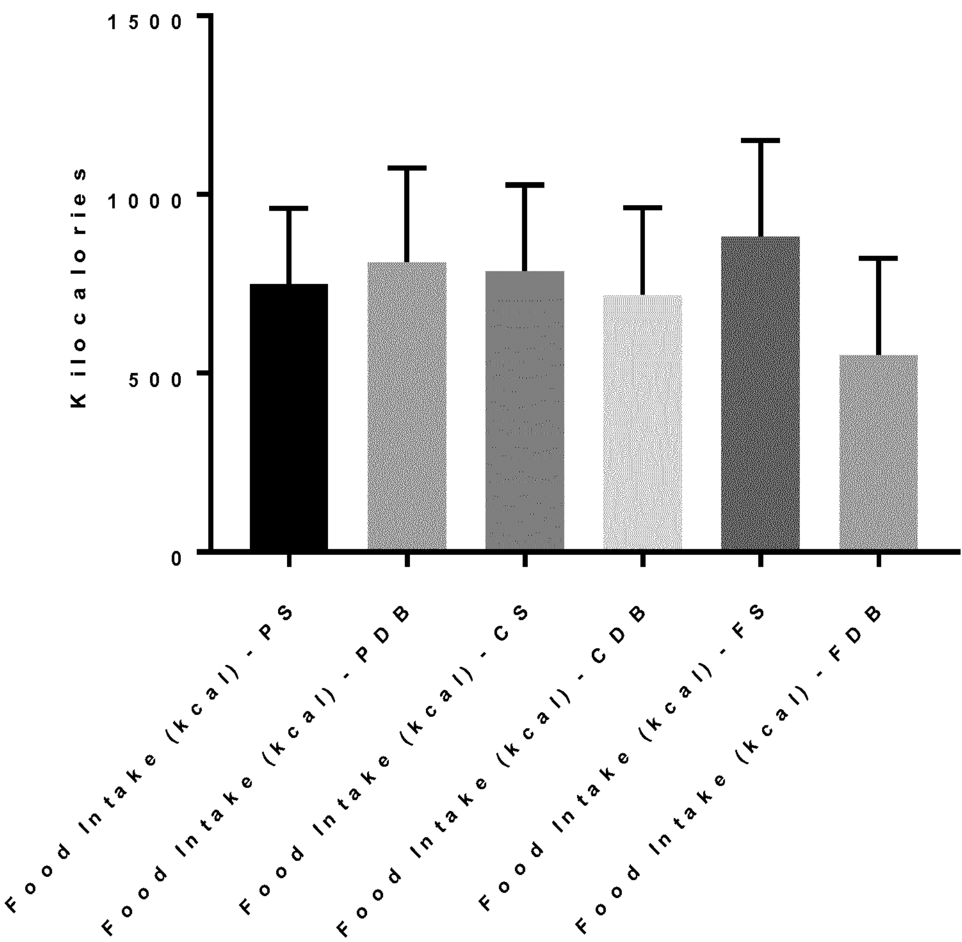
FIG. 10: Total Ad libitum food intake for microencapsulation of all macronutrients delivered to the stomach and distal bowel following ingestion of a micro-particulated test drink containing the relevant macronutrient of interest. Total Ad libitum food intake 180 min after ingestion of micro-particulated test drink (micro-encapsulated macronutrient for targeted delivery to the distal ileum) and a control drink (macronutrient for targeted delivery to the stomach). Ingestion took place after overnight fasting. Results indicate significantly ($P<0.05$) reduced food intake following distal bowel delivery of fat compared to protein or carbohydrate.

FIGS. 9 and 10 illustrate no difference in PYY response or food intake and feeling of hunger when carbohydrate microcapsules were released in the stomach or distal bowel. While a study in rats found that ileal infusions of glucose reduced food intake more than duodenal glucose (Woltman and Reidelberger, 1995), there have been no extensive studies comparing release locations in humans.

Plasma Total PYY Levels

Delivery of lipid in an encapsulated form caused a greater than 50% increase in plasma total PYY levels in the subject (AUC PYY) compared with the control product configured for gastric release (FIGS. 4 and 5). PYY is well-documented for its presence throughout the small intestine, with low concentrations found in the duodenum (6 pmol/g) and considerably higher concentrations in the ileum (84 pmol/g) (Adrian et al., 1985). Fat can induce the release of PYY either indirectly via CCK release in the proximal gut (McFadden et al., 1992) or by directly stimulating the L cells in the distal gut (Aponte et al., 1988). These effects have been related to the activation of the ileal brake mechanism, which acts to further inhibit food intake when nutrients, particularly fat, reach the distal small intestine (Lin et al., 1996). Lin et al. showed that intestinal transit is more powerfully inhibited by the fat-induced ileal brake than by the jejunal brake (Lin et al., 1997). Indeed, several studies have implicated PYY as a primary mediator of the ileal brake (Pironi et al., 1993; Van Citters and Lin, 2006). With fat being the most potent stimulant for the release of PYY, it follows that its delivery to the distal small bowel, where it activates the ileal brake, would induce a larger reduction in food intake and feeling of hunger than if it were delivered to the proximal GIT. This is the effect robustly observed in present study, as per FIGS. 4 and 5.

Feeling of Hunger

Feeling of hunger was not found to be significantly different between the stomach and distal bowel, in any of the macronutrient groups, despite significantly higher PYY concentrations and lower consumption of the ad libitum meal when fat was released in the distal bowel.

GI Symptoms

Mean scores for pain, bloating, flatulence, nausea and urge to defecate and headache did did differ between the ingestion of micro-encapsulated lipid targeted for the distal bowel relative to delivery to the stomach. Subjects experienced diarrhea after micro-particulated lipid targeted for the distal bowel, while no effects were reported for micro-particulated lipid targeted for the stomach. These treatments had a 500 kcal load. The effects of 100 kcal loads are yet to be considered.

Dumping Syndrome

While fat delivered to the distal bowel significantly enhanced PYY secretion and reduced food intake, adverse effects were observed following the consumption of these microcapsules, including several symptoms of dumping syndrome such as abdominal cramping, nausea, diarrhea, vomiting and fatigue. Dumping syndrome is a frequent complication in patients following bariatric surgery, and is related to rapid fluid shifts from the blood into the intestinal lumen, and the release of gut hormones (Ramadan et al., 2016; van Beek et al., 2017).

Example 2

When a dose of encapsulated lipid made according to the methods described in Example 1 but containing 500 Kcal of lipid was delivered to the ileum via the oral route, strong bowel movements were initiated with 60-120 minutes of ingestion of the lipid in 8 out of 9 subjects. Without being bound by theory, it is believed that the strong bowel movements are initiated because the lipid is not absorbed in the ileum due to lack of bile in the ileum. Bile secretion is normally triggered by the presence of lipid in the stomach. With the method of the present invention, as the lipids are not released in the stomach, bile secretion by the subject is not initiated, resulting in a lack of bile in the ileum when the lipid is released.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A method of reducing food intake in a healthy mammal in need of reducing food intake, the method comprising administering to the healthy mammal an oral composition comprising gut peptide hormone response-generating microparticles, in which the microparticles comprise lipid contained within a gastric-resistant, ileal-sensitive carrier, wherein the composition is orally administered 1-3 hours prior to a meal, and in which the carrier comprises a double-coating of denatured crosslinked plant or dairy protein configured for distal bowel release, and wherein administering the composition to the healthy mammal generates a gut peptide hormone response, thereby reducing food intake in the healthy mammal.

2. A method according to claim 1, in which the composition comprises 100-400 Kcal of lipid, in which the lipid is contained within the microparticles.

3. A method according to claim 1, in which the microparticles have a core-shell morphology in which the shell comprises the double-coating of denatured crosslinked plant or dairy protein surrounding a lipid core.

4. A method according to claim 3, in which the lipid core consists essentially of lipid.

5. A method according to claim 1, in which the composition comprises 100-400 Kcal of lipid, in which the lipid is contained within the microparticles.

6. A method according to claim 3, in which the lipid core consists essentially of lipid and the composition comprises 100-400 Kcal of lipid.

7. A method according to claim 1, in which the microparticles are produced by fluidised bed drying or via atomisation of liquid particles at elevated temperatures.

8. A method according to claim 1, in which the microparticles are produced by micro-nozzle co-extrusion.

9. A method according to claim 1, in which the microparticles have an average dimension of less than 500 microns as determined by laser diffractometry.

10. A method according to claim 1, in which the microparticles have an average dimension of less than 200 microns as determined by laser diffractometry.

11. A method according to claim 1, in which the composition is selected from a food supplement, a food product, or a beverage.

12. The method according to claim 1, in which the lipid comprises a monounsaturated fatty acid.

13. The method according to claim 1, in which the lipid comprises fatty acids rich in oleic oil.

14. A method of reducing food intake in a healthy mammal in need of reducing food intake, the method comprising administering to the healthy mammal an oral composition comprising gut peptide hormone response-generating microparticles, in which the microparticles comprise lipid contained within a gastric-resistant, ileal-sensitive carrier, wherein the composition is orally administered 1-3 hours prior to a meal, and in which the carrier comprises a double-coating of denatured crosslinked plant or dairy protein configured for distal bowel release, wherein administering the composition to the healthy mammal generates a gut peptide hormone response, thereby reducing food intake in the healthy mammal and wherein the microparticles are formed by a method comprising the steps of:

providing solid lipid microparticles on a fluidised bed;

spraying a denatured protein solution onto the bed to coat the lipid particles and form microparticles; and drying the microparticles, wherein a second denatured protein solution is sprayed on to the dried microparticles.

* * * * *